(12) United States Patent
Herrmann et al.

(10) Patent No.: US 6,572,748 B1
(45) Date of Patent: Jun. 3, 2003

(54) REFERENCE ELECTRODE

(75) Inventors: Sigrun Herrmann, Waldheim (DE); Heiner Kaden, Waldheim (DE); Wolfram Oelssner, Dresden (DE); Günter Igel, Teningen (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/623,839
(22) PCT Filed: Mar. 3, 1999
(86) PCT No.: PCT/EP99/01369
§ 371 (c)(1), (2), (4) Date: Nov. 26, 2001
(87) PCT Pub. No.: WO99/46586
PCT Pub. Date: Sep. 16, 1999

(51) Int. Cl.⁷ .............................................. G01N 27/26
(52) U.S. Cl. .................. 204/435; 204/433; 204/412; 204/415; 204/419; 204/408; 205/787.5; 205/775
(58) Field of Search ................ 204/435, 433, 204/412, 408, 415, 419; 205/775, 787.5

(56) References Cited

U.S. PATENT DOCUMENTS

| | | | |
|---|---|---|---|
| 4,404,065 A | 9/1983 | Matson | 204/412 |
| 4,536,274 A | 8/1985 | Papadakis et al. | 204/433 |
| 4,933,048 A | * 6/1990 | Lauks | 204/435 |
| 5,368,706 A | 11/1994 | Bowers et al. | 204/435 |
| 5,702,575 A | 12/1997 | Foos et al. | 204/435 |

FOREIGN PATENT DOCUMENTS

| | | |
|---|---|---|
| DE | 19641777 A1 | 4/1998 |
| EP | 0651248 A2 | 5/1995 |
| EP | 0767257 A2 | 4/1997 |
| GB | 2023846 A | 1/1980 |
| GB | 2078962 A | 1/1982 |

* cited by examiner

Primary Examiner—Bruce F. Bell
(74) Attorney, Agent, or Firm—Volpe and Koenig, P.C.

(57) ABSTRACT

A reference electrode (1) for electrochemical measurements includes a metallic palladium-containing electrode component (3) which is covered by a layer (4) formed of or containing a palladium compound poorly soluble in aqueous media. Positioned on layer (4) is a reference electrolyte (5) which contains anions of this palladium compound in dissolved form (FIG. 4).

14 Claims, 3 Drawing Sheets

| | | |
|---|---|---|
| □ SiO₂/Poly-Si/SiO₂ | ▨ Pd | ▨ Pd/PdJ₂ |

| | | | | |
|---|---|---|---|---|
| ▤ Al | □ Si/Poly-Si | ▨ Au | ▨ Ti/Pt | ▨ Ag/AgCl |

REFERENCE ELECTRODE

BACKGROUND OF THE INVENTION

The present invention concerns a reference electrode for electrochemical measurements.

It is known to provide reference electrodes in electrochemical measuring circuits as an electrical reference point in a medium to be investigated. Reference electrodes are reversible nonpolarizable half-cells which form the most constant possible potential substantially independent of the components of the medium to be investigated.

The primary reference electrode in electrochemical measuring technology is the standard hydrogen electrode, whose potential is by definition set equal to zero at all temperatures. In practice, however, one uses almost exclusively electrodes of a second type as reference electrodes since these are easier to handle. They consist essentially of a metal which is coated with a layer consisting of a poorly soluble compound of this metal and is immersed in a solution containing a soluble compound with the anion present in the layer [F. Oehme: Ion-Selective Electrodes, Dr. Alfred Huthig Verlag, Heidelberg 1986, p. 67]. Most widespread are reference electrodes of the type Ag/AgCl, Cl, and $Hg/Hg_2Cl_2$. The standard potentials of these reference electrodes are precisely known so that the potentials measured therewith can be easily converted to the potential of the standard hydrogen electrode [K. Schwabe: Physical Chemistry. Volume 2: Electrochemistry. Akademie Verlag, Berlin 1975, p. 177]. Since the mentioned reference electrodes are universally applicable and exhibit high potential constancy, other metallic electrode materials have only slight importance in electrochemical reference electrodes compared to the mentioned metals silver and mercury.

From Lambrechts, M. et al., Biosensors: Microelectrochemical Devices, Katholieke Universiteit Leuven, Institute of Physics Publishing, Bristol, Philadelphia and New York (1992), page 165, one already recognizes a reference electrode of the type mentioned above which exhibits on a substrate of semiconductor material a layer of metallic silver and, on the latter, a layer of silver chloride. However, this reference electrode has the disadvantage that the silver chloride is photosensitive and can be reduced to metallic silver through the action of light. In order to avoid destruction of the reference electrode through the action of light, suitable protective measures are consequently required. Combined with the prior-art reference electrode is a working electrode of gold, which is connected with the reference electrode to form an electrochemical measuring circuit. Working and reference electrodes are arranged on a common substrate. A disadvantage of this electrode arrangement consists, however, in the fact that the reference and working electrodes are produced from different metallic materials, namely from silver and gold, which requires the application of additional lithographic masks in the production of the reference electrode using planar technology.

SUMMARY

The object therefore is to create a reference electrode of the above-noted type in which the previously mentioned disadvantages are avoided.

The solution to this problem lies in the fact that the reference electrode has an electrode component exhibiting metallic palladium, in the fact that this electrode component is covered by a layer which consists of or contains a palladium compound poorly soluble in aqueous media, and in the fact that a reference electrolyte containing anions of this palladium compound in dissolved form is positioned thereon.

A working electrode of palladium can then be combined with the electrode component in an electrochemical measuring circuit such that the reference and working electrodes can be produced from the same metallic starting material. Thus, for example, the electrode component of the reference electrode can be a palladium wire coated with a compound of palladium that is poorly soluble in aqueous media and immersed in an aqueous or gel-like medium containing anions of the palladium compound. An uncoated palladium wire can then be provided as the working electrode. Additionally advantageous is the fact that the reference electrode according to the present invention is highly insensitive to light. Consequently, lightproof shielding of the reference electrode can be foregone.

To be sure, the use of palladium as sensor material is already known from Lundström, I., et al., Hydrogen-sensitive MOS field effect transistor, Appl. Phys. Lett. 26 (1975), p.55–67, for a different kind of hydrogen-sensitive gas sensor. If, in a MOS field effect transistor, the metal on the gate insulator $SiO_2$ is replaced by a thin layer (<100 nm) of palladium, hydrogen atoms diffuse from the surroundings through this layer to the $Pd/SiO_2$ phase interface, through which the work function in the palladium layer is changed and a measurable shift occurs in the threshold voltage of the field effect transistor. The prior-art hydrogen-sensitive gas sensor, however, exhibits an entirely different configuration compared to the reference electrode of the present invention and does not serve in obtaining a reference potential.

It has also already been attempted to use palladium in producing industrial hydrogen electrodes as type-one electrodes for pH measurement in hydrofluoric acid-containing etching baths, these electrodes being based on the idea that palladium can take up hydrogen in larger amounts [Jasinski, R., A Palladium Hydride pH Electrode for Use in Buffered Fluoride Etch Solutions, J. Electrochem. Soc. 121 (1974), p. 1579–1584]. However, the service lives of such electrodes are short. For this reason, they have not attained any technical importance up to now [Galster, H., pH measurement, VCH Verlagsgesellschaft, Weinheim (1990), p.69; Shao, M. et al., pH measurements based on a palladium electrode, Electroanalysis 6 (1994), p. 245–249].

The palladium/hydrogen system is also specified in U.S. Pat. No. 4,404,065 as reference system in miniaturizable design, e.g., for coulometric sensors in flow processes or for amperometric sensors of thin-layer design. In spite of the advantage that this reference system is applicable up to high pressures (>4 Mpa), its applicability is substantially limited as a result of the fact that pronounced pH sensitivity occurs.

Also already known from GB-A-2 023 846 is a reference electrode with an electrode component of metallic palladium which is covered by a layer of palladium oxide standing in contact with the reference electrolyte. This reference electrode also exhibits a pronounced dependence of its electrode potential on the pH value of the reference electrolyte.

Also already described in U.S. Pat. No. 4,536,274 is a sensor for transcutaneous measurement of the $CO_2$ content in blood. The sensor exhibits a measuring electrode with an electrode component of metallic palladium, which is covered by a layer of palladium oxide. Via the measuring electrode, the $CO_2$ content is indirectly determined through measurement of the pH value. A silver/silver-chloride electrode is assigned as a reference electrode to the measuring electrode. The electric potential at the palladium/palladium-oxide electrode varies as a function of the pH value of the electrolyte standing in contact with the electrode while the potential of the reference electrode remains constant independent of the pH value.

In an especially advantageous embodiment of the present invention, the palladium electrode component is formed as a layer positioned on a substrate formed of semiconductor material, the electrode component particularly being applied to the substrate using a semiconductor-technology production process. The reference electrode can then exhibit especially small dimensions. Beyond this, in producing the reference electrode, additional structures can also be introduced into or applied onto the substrate via the semiconductor-technology production process, for example, structures for an evaluation device for processing a measurement signal, a working electrode, a sensor, and/or similar components. Here, an applied metallization for producing the palladium electrode component on the substrate or the layers found thereon can also be simultaneously utilized in forming a palladium structure for an additional component. The layer containing the poorly soluble palladium salt can be very effectively and economically applied since a large number of electrode structures simultaneously prepared in one production step can be located on one wafer.

The palladium electrode component can be applied especially advantageously via the process known from DE 196 41 777 A1. Here, a structure is produced on the substrate for the palladium electrode component formed of a material with predetermined adhesive properties for metallic palladium. One subsequently undertakes palladium metallization of the surface of the configuration exhibiting the structure in which the palladium metallization remains adhering only to the structure for the palladium electrode component. In this way, the palladium electrode component can be applied to the substrate or the structure located thereon without the use of an additional photolithographic varnish mask. As a result, it is particularly possible to combine the process steps required for the production of the reference electrode in one CMOS process.

In another embodiment of the present invention, the palladium electrode component is formed as a layer which is located on a substrate consisting of ceramic, glass, glass ceramic, printed-circuit-board material, polymeric material, or similar dielectric material and which is particularly applied to the substrate via thick-film technology. The reference electrode can then be produced especially economically, for example, using screen or stencil printing.

It is advantageous if the electrode component contains metallic palladium embedded in finely distributed form in a binder of polymeric material or cermet. In manufacturing the reference electrode, the palladium can be applied to the substrate in a pasty or liquid medium, for example, via screen or stencil printing. The medium can subsequently be hardened, dried, or solidified.

The poorly soluble palladium compound can contain palladium iodide, palladium bromide, and/or palladium acetate. The palladium compound can then be produced simply and economically via electrochemical methods. Here, it is even possible for the layer exhibiting the poorly soluble palladium compound to be deposited or produced electrolytically and/or through a chemical precipitation process in situ on the palladium electrode component.

In an advantageous embodiment of the present invention, anions of the poorly soluble palladium compound are contained in an ionogenic solution and/or a solidified gel. Here, the ion-containing solution and/or the solidified gel can possibly be enclosed between an ion-permeable membrane and the metallic palladium layer.

In an advantageous embodiment of the present invention, the reference electrode is integrated on a semiconductor chip or in a hybrid-structured microsystem. The microsystem, of for example, can exhibit a substrate on which the reference electrode and further components such as, e.g., an evaluation device and/or an ion-selective working electrode can be positioned. Here, the individual components can be mounted on the substrate using in themselves known microtechnological methods. Overall, one consequently obtains a compactly structured measuring device.

The electrode component and/or the layer exhibiting the palladium compound poorly soluble in aqueous media can have a ring-shaped or disk-shaped design or exhibit a rectangular shape. Use of the present invention is not limited to a planar reference electrode. A cylindrical reference electrode can also be advantageously produced by immersing a palladium wire coated with a palladium compound poorly soluble in aqueous media in an aqueous or gel-like medium containing anions of the palladium compound.

It is especially advantageous if the reference electrode is part of an electrochemical measuring system with at least one working electrode located on the substrate and formed especially of palladium and/or part of an ion-sensitive field effect transistor and if the working electrode and/or the field effect transistor is preferably positioned on the front side of the substrate opposite the palladium electrode component. As a result, a particularly compactly structured electrochemical measuring device is obtained in which the reference and the working electrode and/or the field effect transistor are located on the same substrate. Since the working electrode can be formed of palladium just like the electrode component, the working electrode and the electrode component can be applied to the substrate and/or the layers located thereon in a single operation. The electrochemical reference system can then be produced especially economically.

Appropriately, at least one temperature sensor is positioned on the substrate. Any influence of the ambient temperature and/or the temperature of the medium to be investigated on the reference potential of the reference electrode can then compensated for or otherwise taken into consideration.

The reference system of the present invention is preferably employed as a reference electrode in an amperometric sensor. For use as a reference electrode in a potentiometric measuring circuit, the reference electrolyte containing the anions of the palladium compound in dissolved form can be covered with a membrane or surface layer perforated at only one point, with precisely this point being closed off by a diaphragm conventionally used for electrochemical measurements, for example, by a porous membrane or a cation-exchange membrane, while remaining permeable to an electrolytic compound. The membrane is preferably chemically inert, electrically insulating, and/or liquid-tight.

Further advantageous embodiments of the present invention are described in the subclaims.

BRIEF DESCRIPTION OF THE DRAWINGS

In the following, examples of embodiments of the present invention are described in more detail on the basis of the drawings. These include.

DETAILED DESCRIPTION OF THE PREFERRED EMBODIMENT(S)

Figure 1:
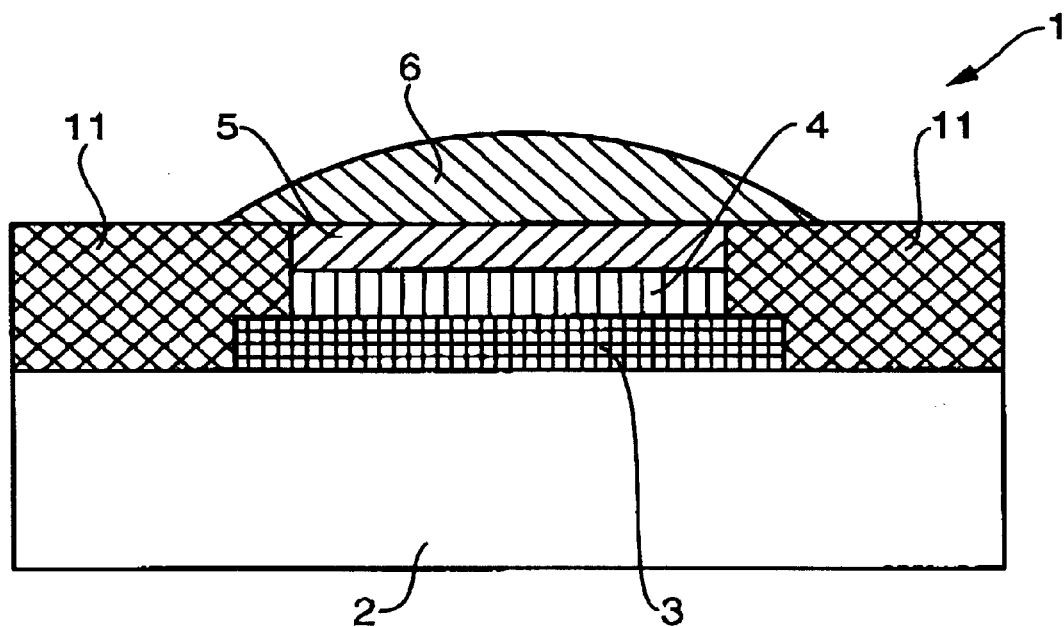
FIG. 1 a cross-section through a reference electrode for amperometric measurements, FIG. 2 a cross-section through a reference electrode for potentiometric measurements, FIG. 3 a cross-section through the reference electrode for amperometric measurements shown in FIG. 5 along the cross-sectional plane designated by I in FIG. 5, FIG. 4 a representation similar to FIG. 2, the reference electrode, however, being integrated in a semiconductor chip, and FIG. 5 a top view of a reference electrode for amperometric measurements, the reference electrode being integrated in a semiconductor chip and the reference electrolyte and the surface layer being represented as transparent.

A reference electrode for electrochemical measurements designated as a whole by 1 includes a substrate 2 formed of semiconductor material or a dielectric material. Positioned on the substrate 2 is a palladium electrode component 3 formed by a thin layer of metallic palladium. The palladium electrode component 3 is covered by a layer 4 formed of a palladium compound poorly soluble in aqueous media. On the side of the poorly soluble layer 4 opposite the palladium electrode component 3, one finds next to the poorly soluble layer 4 a reference electrolyte 5 which contains anions of the palladium compound of layer 4 in dissolved form. On the side of the reference electrolyte 5 opposite the poorly soluble layer 4, the medium being investigated 6 borders on the reference electrolyte 5.

Figure 2:
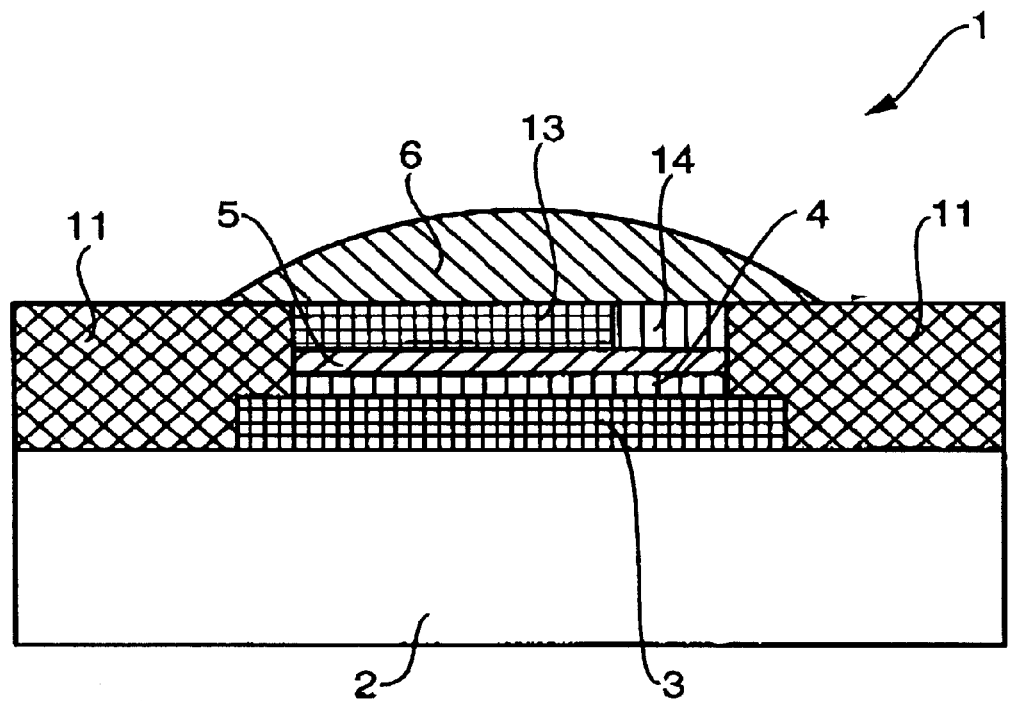
Figure 3:
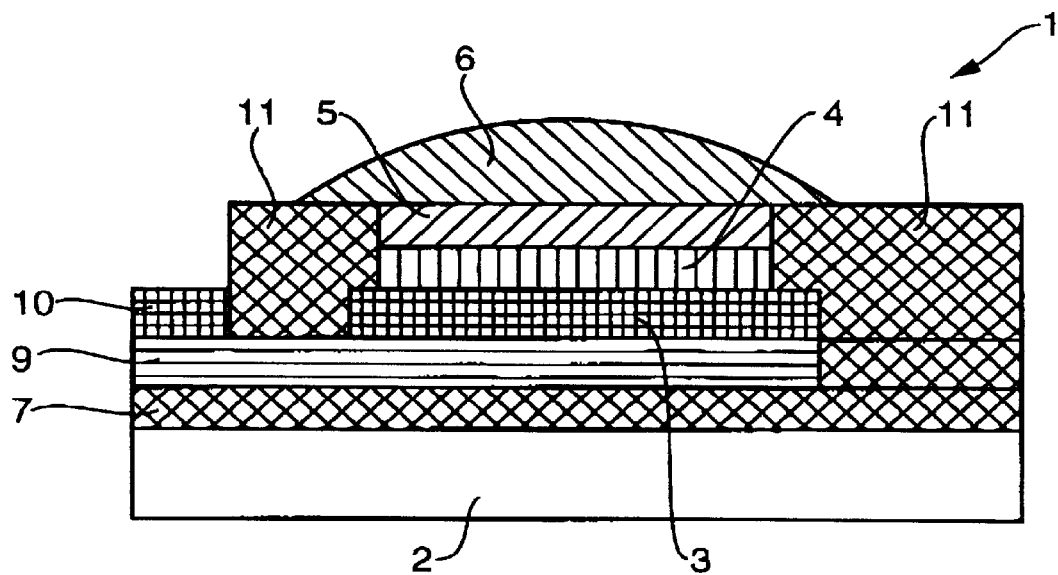
Figure 4:
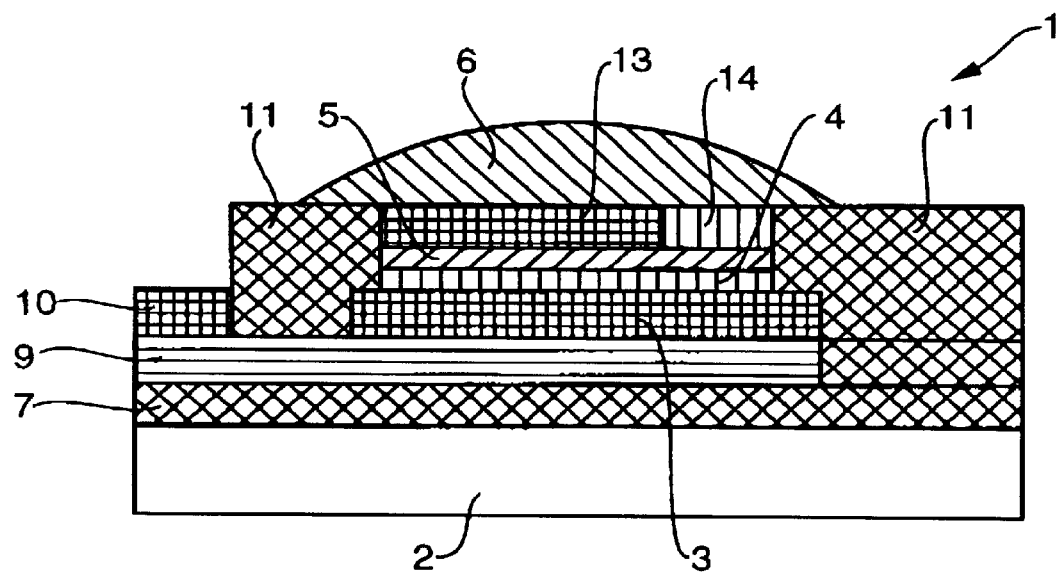

In the embodiments according to FIGS. 3 and 4, the substrate 2 is a silicon semiconductor chip on whose surface a passivation layer 7 is positioned, which, for example, can exhibit a silicon dioxide layer or a CVD (chemical vapor deposition)-applied silicon nitride layer. The semiconductor chip additionally exhibits transit paths 9 which can be prepared, for example, from polysilicon using the thin-film technique. The palladium electrode component 3 is likewise applied via the thin-film technique to the provided point on a polysilicon transit path 9. The shape and size of the palladium electrode component 3 can be selected over wide limits. In the embodiments according to FIGS. 1 and 2, the palladium electrode component 3 has the form of a ring-shaped segment with an area of 0.16 mm². The polysilicon transit path 9 produces the electrical connection of the palladium electrode component 3 to a palladium-coated bond point 10, which makes possible contact to the outside.

The palladium electrode component 3 is laterally surrounded by an insulating layer 11 which at least partly covers the palladium electrode component 3. The insulating layer 11 exhibits a break or opening exposing a specific point of the palladium electrode component 3. The insulating layer 11 can be, for example, a CVD oxide layer applied in structured fashion. In manufacturing the reference electrode 1, this forms the substrate for the further buildup of the reference electrode 1.

In order to complete the reference electrode 1 of the second type, there is positioned on the palladium electrode component 3 a layer 4 of palladium iodide ($PdI_2$) substantially insoluble in aqueous medium, which can be produced, for example, through electrochemical iodization in 0.1 M KI solution at a potential of 700 mV against a saturated AG/AgCl electrode. In order to improve the adhesion of this electrolytically produced layer 4, an intermediary layer of finely distributed palladium is positioned on the palladium layer 3. In manufacturing the reference electrode 1, the intermediary layer can, for example, be galvanically deposited from a weakly acidic (pH=5.6–6.5) palladium bath using a palladium anode at a current density of 40 $\mu A/mm^2$ and room temperature over a period of about 5 minutes. The palladium bath can contain, for example, 5–10 g/l palladium chloride, 15–20 g/l sodium nitrite, 40–50 g/l sodium chloride, and 25–30 g/l boric acid.

The $PdI_2$ layer 4 produced in this way is covered with the reference electrolyte 5 exhibiting the anions of the palladium compound contained in layer 4. The reference electrolyte 5, for example, can be a solution containing 0.1 M hydriodic HI acid.

In a variation, the reference electrolyte 5 according to FIGS. 1 and 3 can also be a hydrogel formed from 2 g HEMA, 60 mg tetraethyleneglycolmethacrylate, 80 mg dimethoxyphenylacetophenone, and 12 mg poly-N-vinylpyrrolidone crosslinked via UV irradiation. Introduced into the hydrogel is an electrolyte which can consist, for example, of a mixture of water and ethylene glycol in a ratio of 1:9 containing sodium bicarbonate, sodium carbonate, and potassium iodide, each at a concentration of 0.1 m/l.

As a result of the contact of the $PdI_2$ layer 4 with the electrolyte 5 formed by the solution or the gel, a constant potential, namely the reference potential, develops. This reference potential depends on the concentration of the anion (e.g., iodide) of the palladium compound in the reference electrolyte 5 or gel.

In the case of the embodiments shown in the drawings, the layer 4 exhibiting the poorly soluble palladium compound can also be chemically deposited current-free at 50° C. on the surface of the palladium electrode component 3 from an alcohol iodine solution containing 1 g iodine in 10 ml ethanol. In a modification, the layer 4 is likewise chemically deposited on the palladium electrode component 3, in this case, however, using an aqueous solution of palladium chloride $PdCl_2$ and hydriodic acid HI.

In the embodiments according to FIGS. 1 and 2, the reference electrode 1 according to the present invention is produced viathick-film technology. The nonconducting substrate 2 is a commercial hard glass-fiber-reinforced epoxy resin fabric or a ceramic plate. Located on the substrate 2 is a hardened palladium-filled epoxy resin paste applied via screen printing; this forms the electrode component 3 according to FIGS. 3 and 4. The insulating layer 11 serving in encapsulation consists of a polymeric insulating paste applied via screen printing. The ring-shaped structure of the reference system is also formed by this layer. Layer 4 with the poorly soluble palladium compound is, according to the embodiment shown in FIGS. 3 and 4, deposited electrolytically or applied in the thick-film process as a thick-layer paste filled with palladium iodide. The reference electrolyte 5 corresponds to that of the embodiment according to FIGS. 3 and 4.

An advantageous application of the inventive reference system as a reference electrode for amperometric measurements is shown in FIGS. 1 and 3. Here, the reference electrode, which is formed by the substrate 2, the palladium electrode component 3, layer 4 involving the insoluble palladium compound, and the reference electrolyte 5 (which can be, for example, a gel), is in contact with the medium being analyzed 6. The insulating layer 11 seals the palladium electrode component 3, layer 4, and the reference electrolyte 5 with respect to the medium being analyzed 6 such that only a limited surface area of the reference electrolyte 5 is in direct contact with the medium being analyzed 6. In the case of amperometric measurements, one finds in the medium being analyzed 6 in addition to the reference electrode 1 of the present invention at least one further electrode, namely a measuring or working electrode 12, which is connected with the reference electrode 1 to form a measuring circuit. Reference electrode 1 can function in this measuring circuit both as a reference electrode and also as a counterelectrode.

Figure 5:
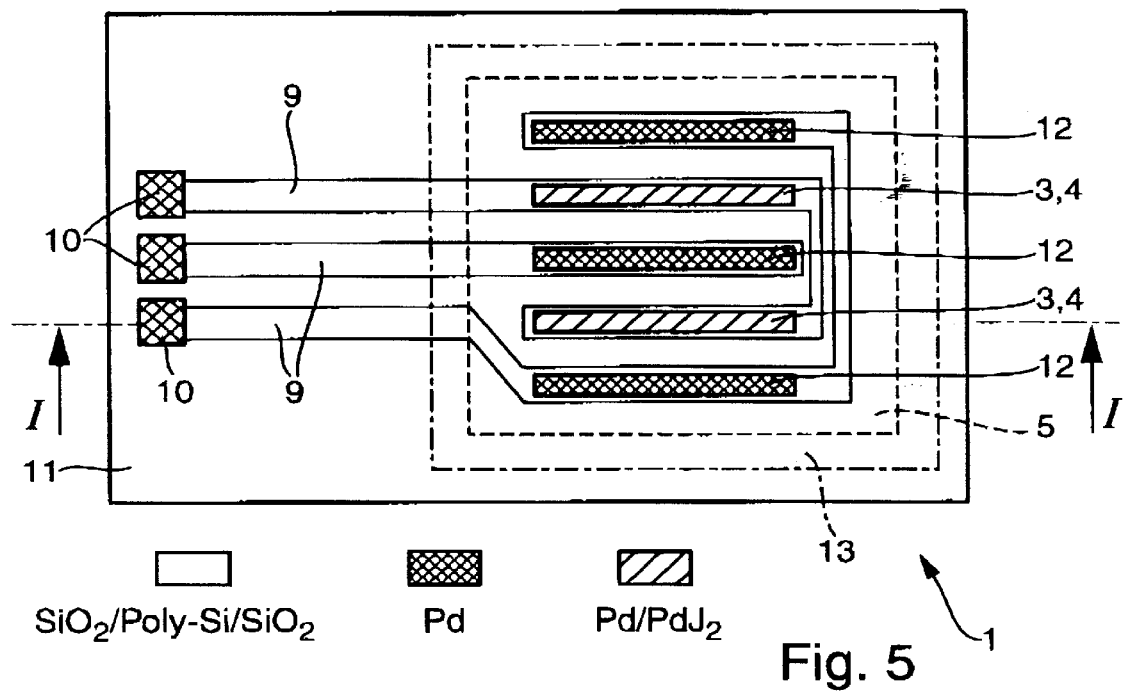

FIG. 5 shows an embodiment in which several working electrodes 12 are arranged together with two reference electrodes 1 on a common substrate. In advantageous fashion, the working electrodes 12 and/or the bond points 10 can likewise be formed of palladium so that the entire measuring arrangement shown in FIG. 5 can be produced in simple fashion via methods of semiconductor technology using only a few materials, preferably employed in semiconductor technology. In manufacturing the measuring arrangement using planar technology, only relatively few masks therefore need to be applied to the substrate or the structures or layers already found thereon.

Figure 6:
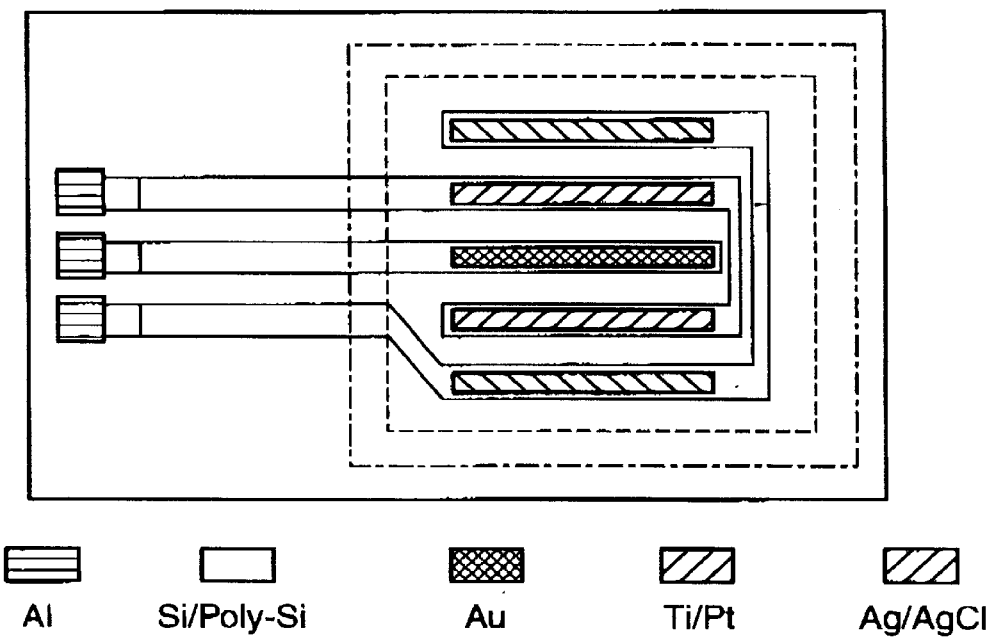
FIG. 6 a top view of a reference electrode in accordance with the prior art.

For comparison, a measuring arrangement known from the state of the art is shown in FIG. 6. Clearly recognizable is the fact that this measuring arrangement exhibits substantially more materials than that according to FIG. 5. Production of the prior art measuring arrangement is therefore relatively complicated and expensive.

FIGS. 2 and 4 show schematically a reference electrode 1 for potentiometric measurements. In addition to the layers of the reference electrode 1 according to FIGS. 1 and 3, the reference electrode 1 according to FIGS. 2 and 4 further exhibits a membrane or surface layer 13, which is positioned between the medium being analyzed 6 and the reference electrolyte 5 and separates the latter from the medium being analyzed 6 in electrically insulating and liquid-tight fashion. The surface layer 13 is perforated only at a relatively small point and closed at this point by a diaphragm 14. Diaphragm 14 is permeable to liquids and thus insures electrolytic contact of the reference electrolyte 5, which contains the anion of the palladium compound present in layer 4 and can be, for example, a gel or a solution, with the medium being analyzed 6. The diaphragm can be, for example, a ceramic plug or a porous polymer membrane.

In summary, one thus obtains a reference electrode 1 for electrochemical measurements exhibiting a metallic palladium-containing electrode component 3 which is covered by a layer 4 which consists of or contains a palladium compound poorly soluble in aqueous media. Positioned on layer 4 is a reference electrolyte 5 which contains anions of this palladium compound in dissolved form.

What is claimed is:

1. Reference electrode (1) for electrochemical measurements, characterized in that it has an electrode component (3) including metallic palladium, that the electrode component (3) is covered by a layer (4) formed of or containing a palladium compound that is poorly soluble in aqueous media, and that a reference electrolyte (5) containing anions of the palladium compound in dissolved form is positioned thereon.

2. Reference electrode according to claim 1, characterized in that the palladium electrode component (3) is formed as a layer positioned on a substrate (2) formed of semiconductor material and that the electrode component (3) is applied to the substrate (2) using a semiconductor-technology production process.

3. Reference electrode according to claim 1, characterized in that the palladium electrode component (3) is formed as a layer which is positioned on a substrate (2) formed of ceramic, glass, glass ceramic, printed-circuit-board material, polymeric material, or similar dielectric material and which is applied to the substrate (2) via thick-film technology.

4. Reference electrode according to claim 3, characterized in that the electrode component (3) contains metallic palladium embedded in finely distributed form in a binder of polymeric material or cermet.

5. Reference electrode according to one of claim 1, characterized in that the poorly soluble palladium compound of layer (4) contains palladium iodide, palladium bromide, and/or palladium acetate.

6. Reference electrode according to one of claim 1, characterized in that the layer (4) exhibiting the poorly soluble palladium compound is produced electrolytically and/or through a chemical precipitation process in situ on the palladium electrode component (3).

7. Reference electrode according to one of claim 1, characterized in that anions of the poorly soluble palladium compound of layer (4) are contained in an ionogenic solution and/or a solidified gel.

8. Reference electrode according to claim 1, characterized in that the electrode is integrated on a semiconductor chip or in a hybrid-structured microsystem.

9. Reference electrode according to one of claim 1, characterized in that the electrode component (3) and/or the layer (4) have a ring-shaped or disk-shaped design or have a rectangular shape.

10. Reference electrode according to claim 1, characterized in that it is a part of an electrochemical measuring system with at least one working electrode (12) located on the substrate (2) and formed of palladium and/or part of an ion-sensitive field effect transistor and that the working electrode (12) and/or the field effect transistor is positioned on the front side of the substrate (2) opposite the palladium electrode component (3).

11. Reference electrode according to one of claim 1, characterized in that at least one temperature sensor is positioned on the substrate (2).

12. Reference electrode according to claim 1, characterized in that the reference electrolyte (5) containing the anions of the palladium compound in dissolved form is covered with a membrane or surface layer (13) perforated at only one point and this point is closed off with a diaphragm (14) conventionally used for electrochemical measurements, but is permeable to an electrolytic compound.

13. Reference electrode according to claim 12, said diaphragm comprising either a porous membrane or a cation-exchange membrane.

14. Method of establishing a reference potential in an amperometric and/or potentiometric measuring circuit comprising the step of:

providing a reference electrode (1) for electrochemical measurements, characterized in that it has an electrode component (3) including metallic palladium, that the electrode component (3) is covered by a layer (4) formed of or containing a palladium compound that is poorly soluble in aqueous media, and that a reference electrolyte (5) containing anions of the palladium compound in dissolved form is positioned thereon; and, connecting said electrode in the circuit.

* * * * *

UNITED STATES PATENT AND TRADEMARK OFFICE
CERTIFICATE OF CORRECTION

PATENT NO. : 6,572,748 B1
DATED : June 3, 2003
INVENTOR(S) : Herrmann et al.

It is certified that error appears in the above-identified patent and that said Letters Patent is hereby corrected as shown below:

<u>Title page,</u>
Please insert item [30] as follows:
-- [30]     Foreign Application Priority Data
    March 10, 1998    (DE) ...........................198 10 098.1 --

<u>Drawings,</u>
Figure 6, please insert the legend -- Prior Art --.

<u>Column 1,</u>
Line 24, after "Ag/AgCl", delete "Cl", and insert therefor -- Cl⁻ --.

<u>Column 4,</u>
Line 5, delete the word "of".

<u>Column 8,</u>
Lines 9, 13, 18, 25 and 37, delete the phrase "one of".

Signed and Sealed this

Tenth Day of February, 2004

JON W. DUDAS
*Acting Director of the United States Patent and Trademark Office*